United States Patent [19]

Jaworek et al.

[11] 3,969,287

[45] *July 13, 1976

[54] CARRIER-BOUND PROTEIN PREPARED BY REACTING THE PROTEIN WITH AN ACYLATING OR ALKYLATING COMPOUND HAVING A CARRIER-BONDING GROUP AND REACTING THE PRODUCT WITH A CARRIER

[75] Inventors: Dieter Jaworek, Weilheim, Upper Bavaria; Michael Nelböck-Hochstetter, Tutzing; Klaus Beaucamp, Tutzing; Hans Ulrich Bergmeyer, Tutzing; Karl-Heinz Botsch, Bernried, all of Germany

[73] Assignee: Boehringer Mannheim GmbH, Mannheim, Germany

[ * ] Notice: The portion of the term of this patent subsequent to Apr. 23, 1991, has been disclaimed.

[22] Filed: Nov. 30, 1973

[21] Appl. No.: 420,510

[30] Foreign Application Priority Data

Dec. 8, 1972  Germany............................ 2260185

[52] U.S. Cl..................................... 260/8; 195/63; 195/68; 260/112 R
[51] Int. Cl.²......................................... C08L 89/00
[58] Field of Search............... 260/8, 112 R; 195/63, 195/68, DIG. 11

[56] References Cited
UNITED STATES PATENTS

| | | | |
|---|---|---|---|
| 3,574,062 | 4/1971 | Sato...................................... | 260/7.5 |
| 3,619,371 | 9/1971 | Crook et al.......................... | 260/112 |
| 3,759,890 | 9/1973 | Wilson................................. | 260/112 |
| 3,764,477 | 10/1973 | Lehmann............................ | 260/112 |
| 3,775,253 | 11/1973 | Dieter et al............................. | 260/8 |
| 3,788,948 | 1/1974 | Kagedal et al....................... | 260/112 |
| 3,806,417 | 4/1974 | Beaucamp et a. .................. | 260/112 |

OTHER PUBLICATIONS

Chem. Absts., vol. 78: 73970 m; "Enzymically . . . Matrix . . . Protease . . . Surface;" Franks.

*Primary Examiner*—Edward M. Woodberry
*Attorney, Agent, or Firm*—Burgess, Dinklage & Sprung

[57] ABSTRACT

Carrier-bound proteins are prepared by reacting a protein in aqueous solution with a coupling compound having at least one group capable of acylating or alkylating proteins and at least one additional group capable of producing a bond with a carrier material, and reacting the resulting product with a carrier material, optionally forming the carrier material in situ by polymerization of a monomer or monomer mixture in the presence of said product.

17 Claims, No Drawings

CARRIER-BOUND PROTEIN PREPARED BY REACTING THE PROTEIN WITH AN ACYLATING OR ALKYLATING COMPOUND HAVING A CARRIER-BONDING GROUP AND REACTING THE PRODUCT WITH A CARRIER

The present invention relates to a new process for the preparation of carrier-bound proteins, as well as to the proteins bound to water-insoluble carriers obtained according to this process.

The interest in carrier-bound proteins, especially carrier-bound enzymes, is continuously increasing and numerous carrier materials and fixing methods have already been described. However, only a few of the previously known methods and carrier materials give really satisfactory products with a high activity and in good yield and of sufficient stability. Therefore, only a few carrier-bound enzymes have hitherto been commercially available and these are the especially stable proteolytic enzymes. This is particularly due to the fact that the more sensitive enzymes or enzyme complexes either completely lose their activity when fixed by the previously known methods or are so unstable that they cannot be used for technical purposes.

The present invention comprises a process for the preparation of carrier-bound proteins, wherein a protein is reacted in aqueous solution with a compound which contains at least one group capable of acylating or alkylating proteins and at least one further functional group capable of producing a bond with a carrier substance, whereafter this further functional group is reacted with the carrier substance.

The present invention provides an especially mild process for binding proteins to insoluble carriers, which gives products which not only have a high activity and activity yield but which are also, above all, so stable that they can be used for technical purposes. Only by fulfillment of these requirements is it possible technically to utilize the principal property of the enzymatically-active proteins of not being consumed and of being reusable for long periods of time.

As groups which can acylate or alkylate proteins in aqueous solution and which, in the following, are referred to as "coupling compounds", there can be used the numerous groupings known for the purpose, in particular, from peptide chemistry. Preferred acylating or alkylating groups within the meaning of the present invention include, for example, ethylene-imine groups, halide groups activated by unsaturation, acid halide groups, azide groups, acid anhydride groups, aldehyde groups, oxazolone groups, as well as compounds of the general formula R.CO.X, wherein X corresponds to one of the following formulae:

1      —N=NH

2 

3 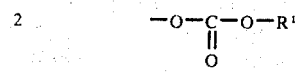

4 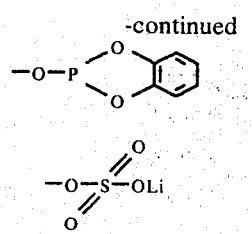

5 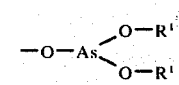

6 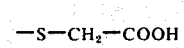

7      —S—CH$_2$—COOH

8      —O—CH$_2$—CN

9 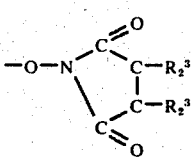

10 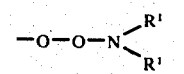

11 

12 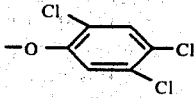

13 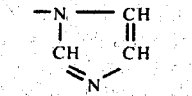

14 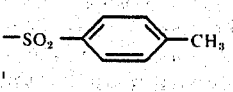

15 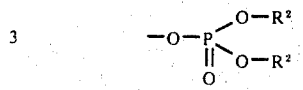

-continued

16 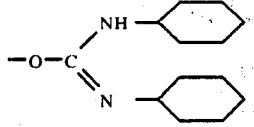

17 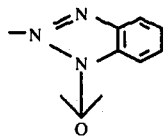

18 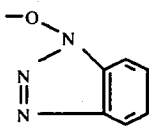

In the above-given general formulae 1 to 18, $R^1$ is an alkyl radical which preferably contains up to 6 carbon atoms, $R^2$ is an aryl or aralkyl radical or a halogen atom, phenyl and benzyl radicals being the preferred aryl and aralkyl radicals, and $R^3$ has the same meaning as $R^1$ or can also be a hydrogen atom. Other examples of acylating and alkylation agents capable of coupling with proteins include the following compounds:

19 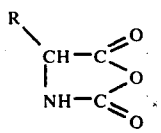

20 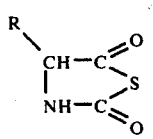

In the above-given two general formulae, R is the residue of a coupling compound which contains a functional group capable of bonding with the carrier.

As further functional groups capable of bonding with a carrier, there are preferably used those groups which undergo an addition or condensation reaction with the actual carrier substance. Insofar as coupling compounds are used with a group capable of condensation, care is to be taken that, in the course of the condensation, no substances are split off which disadvantageously inclucence the activity of the bound protein. Whether the use of a particular group capable of condensation results in the splitting off of a substance which impairs the activity of the enzyme used, can, in each case, be easily determined with regard to a particular protein to be bound by means of a few simple preliminary experiments. General statements with regard to the suitability of particular groups cannot be made since the various active proteins display greatly differing sensitivities. For example, we have found that the splitting off of halides leads to a loss of activity of many sensitive proteins, whereas other active proteins are not disadvantageously affected by halides.

The bonding of the intermediate product with the carrier can be carried out especially gently by polymerizing it into the carrier substance. Therefore, according to the present invention, it is especially preferred to use a coupling compound which contains at least one double bond capable of copolymerization, especially a carbon-carbon double bond, as the further functional group capable of producing a bond with a carrier.

As carrier substances, according to the present invention there can be used all those water-insoluble solid materials which, via the further functional group of the coupling compound, can be coupled therewith in aqueous solution under mild conditions. Preferably, there are used carrier substances which are hydrophilic, easily swellable, substantially charge-free and also stable towards micro-organisms. The carrier substance can be introduced as such into the aqueous solution for the production of the bond with the intermediate product but preferably the carrier substance is itself produced in the aqueous solution by the polymerization of water-soluble monomers. In the case of this preferred embodiment of the process according to the present invention, the reaction of the protein with the coupling compound can take place either in the presence of the polymerizable monomer or monomers, whereafter the polymerization is carried out with the polymerizing in the presence of the coupling compound-protein intermediate product, or the polymerizable monomer or monomer mixture is first added to the solution after the reaction has taken place between the protein and the coupling compound, whereafter the polymerization is initiated.

As monomers for use according to this embodiment of the process according to the present invention, there can be used those water-soluble compounds which are capable of polyaddition or polycondensation. Monomers capable of polyaddition are preferred and especially those monomers which contain at least one olefinic unsaturation. In this case, the further functional group of the coupling compound is preferably also a double bond capable of copolymerization.

Typical examples of preferred coupling compounds according to the present invention include maleic anhydride and its homologues in which the hydrogen atoms of the carbon-carbon double bond are replaced by alkyl radicals containing up to 6 carbon atoms, allyl halides, especially allyl bromide and its homologues, acryloyl chloride and its homologues in which one or more hydrogen atoms are replaced by one or more lower alkyl radicals, maleic acid and fumaric acid chlorides and their homologues corresponding to the above definition in the case of maleic anhydride, maleic acid azide and ethyleneimine compounds, such as 1-allyloxy-3-(N-ethyleneimine)-propan-2-ol and the like.

The monomer used according to the preferred embodiment of the process according to the present invention must, as already mentioned, be water-soluble and, at the same time, contain an olefinic carbon-carbon double bond capable of polymerization. Here, too, there are preferably used compounds containing the Michael system, i.e., with a carbon-carbon double bond adjacent to a carbon-oxygen double bond. As monomers, it is especially preferred to use the water-soluble derivatives of vinyl alcohol, acrylic acid or methacrylic acid, for example, the amides, nitriles or esters of these compounds, especially good results being obtained with the use of acrylamide. The compounds can also be substituted by alkyl radicals so long as the water-solubility of the compounds is not reduced too much. However, such compounds with reduced water-solubility are of advantage if, subsequently, the carrier-bound enzyme is to be used in a system which is not entirely aqueous, for example, in an aqueous-organic system. The corresponding derivatives of maleic and fumaric acids can also be satisfactorily used.

Alternatively, there can also be water-insoluble monomers. In this case, the polymerization is carried out in suspension and not in solution. Suspension polymerization is of advantage if a finely-divided pearl-like matrix which does not swell in aqueous systems is desired. The polymerization spheroids obtained according to the known methods of suspension polymerization (pearl polymerization) then contain on their surface the polymerized on protein-coupling compound addition product.

There can be used a single polymerizable monomer or also a mixture of monomers. It is also possible to use a prepolymer which still contains unsaturated groups, together with a monomer.

Depending upon the desired consistency of the end product, cross-linking agents, i.e. compounds containing more than one polymerizable group, can be added to the monomer. Examples of cross-linking agents of this type include N,N'-methylene-bis-acrylamide and ethylene diacrylate. These are preferred in the case of working in aqueous solution. If the polymerization is carried out in a heterogenous phase, i.e. as a suspension polymerization, there can also be water-insoluble cross-linking agents, for example, divinyl-benzene or ethylene-dimeth-acrylate. Numerous other cross-linking agents are also known to those skilled in the art and the appropriate choice for each particular case will be readily apparent to those skilled in the art. It is also possible subsequently to cross-link carrier-bound proteins obtained by the process according to the present invention, the carrier of which is not cross-linked.

If a cross-linking agent is not used, then the carrier materials are obtained which are soluble or thermoplastic. An embodiment of the process according to the present invention in this form leads to spinnable or extrudable solutions, from which the carrier-bound proteins can be obtained in known manner, for example, in the form of filaments or films. Filaments or films of this type covalently bonded with active proteins can be stretched according to the methods used in synthetic resin technology or can be spun and worked up to give products which contain the bound proteins and can be used for purposes in which these forms offer special advantages, for example, for the production of enzymatically-active sieves, fabrics, implantable filaments and the like.

For spinning from aqueous solutions, there can be used, for example, the vacuum spinning process in which the solution is forced through a spinning nozzle into a vacuum. This can take place under the conditions of lyophilization which can be endured by most active proteins without loss of activity.

It is also important, for the process according to the present invention, that the protein is first reacted with the coupling compound, whereafter the intermediate product obtained is fixed on to the carrier substance. The reaction of the protein with the coupling compound normally needs no special measures. It is usually sufficient to bring the protein and coupling compound together at ambient temperature in aqueous solution. It is hereby expedient to work in a buffered aqueous solution, the pH value of which is appropriate for the protein in question. The period of reaction between protein and coupling compound depends upon the particular substances used but, in general, is between about 5 minutes and 1 hour. Longer or shorter incubation times can, however, also be expedient from case to case.

The reaction of protein and coupling compound can, as mentioned, be carried out in the presence of the carrier or of the starting products for the carrier. In the latter case, the polymerization reaction is expediently initiated, after the formation of the pre-product, by the addition of an initiator. As initiators, there can be used the initiators and catalysts conventionally employed in polymer chemistry insofar as they do not disadvantageously influence the activity of the protein. As initiators or catalysts, there can, for example, be used, in the case of olefinically-unsaturated monomers or prepolymers, inorganic or organic peroxides, azo compounds and the like. In addition, reaction accelerators, such as amines and the like, can be used. When using acrylic acid or methacrylic acid derivatives as monomers, the use of an initiator combination of a peroxydisulfate and an amine, such as 3-dimethylaminopropionitrile, has proved to be especially useful. When using this initiator combination, it is expedient to work under an inert atmosphere, for example under nitrogen.

When the process products are directly formed as insoluble materials, they can be isolated by simple filtering, followed by washing. If the carrier is not cross-linked and remains in solution, the solvent can be removed in the usual way, for example, as mentioned above by vacuum spinning.

The process according to the present invention provides a number of important advantages. Of special importance is that it is possible, according to the present invention, to bind sensitive proteins and protein-containing materials, for example enzymes, which are composed of several subunits, to carriers without great loss of activity. In the case of the previously known methods for fixing sensitive proteins on to carriers, the sensitive proteins were, in almost all cases, deactivated or preparations were obtained of low storage stability and low activity. In contradistinction thereto, the process according to the present invention permits a bonding of sensitive proteins to carriers in an especially gentle manner. Furthermore, by means of the process according to the present invention, there is achieved a certain spatial separation of the bound protein from the actual matrix or carrier substance since the coupling compound is present as intermediate member. In the case of swelling processes and the like, the enzyme or protein bond is thereby protected.

Especially when inorganic carriers, such as glass and oxides or halides of the Sub-Groups elements are used as carriers, there can now be found coupling compounds for almost every case which are able to react not only with the protein but also with the carrier, on the basis of the known reactivities of the functional groups.

Of additional advantages, there are to be mentioned, in particular, the improved yields, the removal of the residual reactive groups on the carrier, which cannot be excluded in the fixing process via activated carriers, absence of undesired ion exchanger properties and thus also of swelling or shrinking in the case of proteins bound according to the process of the present invention, avoidance of heteropolar bonds of the protein to the carrier, avoidance of undesired adsorption properties not only with regard to the substrate but also the reaction product, no undesired displacement of the pH optimum and the like. Improved yields are achieved, especially in the case of fixing proteins with comparatively high molecular weights. For example, an inclusion polymerization of catalase gives a maximum fixing of 10% in acrylamide gel but, in the case of the process according to the present invention, for example with the use of acryloyl chloride as coupling compound, the yield is 75%. Furthermore, an especial advantage of the process according to the present invention is that also proteins consisting of subunits which, because of their sensitivity, cannot be bound to carriers or can only be bound with difficulty to carriers by known methods, can be fixed with good yields and high stbility. Surprisingly, we have also found that the enzymes fixed by the process according to the present invention are more stable than when in the non-bound, soluble form. For example, urease fixed to a carrier according to the process of the present invention and having a molecular weight of 480,000 is still completely active at 70°C, whereas at the same temperature but in an unbound form, it is irreversibly inactivated within an extremely short space of time.

A further substantial advantage of the process according to the present invention is that several enzymes, for example glucose oxidase and catalase, even in the case of differing reactivity and differing molecular weight, can be simultaneously fixed in statistical distribution on to a carrier or can be incorporated therein. This also occurs even when the proteins have different isoelectric points. In especially difficult cases, it is possible to react the different proteins separately with the same or different coupling compounds and then to fix them together on to the carrier. The process according to the present invention is, of course, also suitable for fixing proteins on to formed carriers, for example, on to films, tubes, rods, plungers and the like.

The following Examples are given for the purpose of illustrating the present invention:

EXAMPLE 1

100 mg glucose oxidase (GOD; 220 U/mg) were dissolved in 10 ml 1M triethanolamine buffer (pH 8.0) at 10°C under an atmosphere of nitrogen. 0.03 acryloyl chloride in 3 ml ether were then added thereto and the reaction mixture was stirred for thirty minutes. Subsequently, it was dialyzed overnight against 2 liters 0.01M triethanolamine buffer (pH 8.0) and then the precipitate was centrifuged off and discarded. The enzymatic activity amounted to 16,000 U.

The solution thus obtained was then mixed with 0.4 ml 5% dimethylaminopropionitrile and 0.4 ml 5% ammonium peroxydisulfate at 5° to 10°C (enzymatic activity 14,500). Thereafter, 3 g acrylamide and 0.015 g N,N'-methylene-bis-acrylamide in 9 ml water were added under an atmosphere of nitrogen. The polymerization which commenced immediately led to a gel-like solidification of the mass. The product obtained was granulated by forcing through a 0.4 mm metal sieve and then washed with two liters 0.2M phosphate buffer (pH 7.5). The enzymatic activity removed with the wash water was 600 U. The polymer was lyophilized to give 3 g of dry product with an enzymatic activity of 1500 U.

When the process was repeated but without the use of acryloyl chloride, the inclusion polymerization gave 3 g of a product with a total activity of 330 U.

EXAMPLE 2

300 mg trypsin (1500) were dissolved, under an atmosphere of nitrogen, in 10 ml 0.5M phosphate buffer (pH 8.0) at 10°C. The solution obtained was mixed with 0.1 ml acryloyl chloride in 10 ml ether and the reaction mixture was stirred for thirty minutes. There were then added 0.4 ml 5% dimethylaminopropionitrile and 0.4 ml 5% ammonium peroxydisulfate and the reaction mixture stirred for 30 minutes. Subsequently, 3 g acrylamide and 0.015 g N,N'-methylene-bis-acrylamide in 9 ml water were added under an atmosphere of nitrogen at a temperature of 5° to 10°C and these conditions were maintained until a gel-like solid mass had formed. This mass was granulated by forcing through a 0.4 mm metal sieve and washed with 3 liters of 0.2M phosphate buffer (pH 7.5). 23 U of enzyme activity were found in the wash water. The washed produce was lyophilized. There were obtained 3 g lyophilizate with a specific activity of 12.9 U/g.

A repetition of the process under the same conditions but without the addition of the acryloyl chloride gave a specific activity of 0.5 U/g of lyophilizate.

EXAMPLES 3 – 12

As described in Example 1 and using acryloyl chloride, maleic acid azide, maleic anhydride, allyl bromide and 1-allyloxy-3-(N-ethyleneimine)-propan-2-ol as coupling compound, there was carried out the fixing of the enzymes glucose oxidase, trypsin, chymotrypsin, uricase and hexokinase. In the same way, the process was repeated but without using the coupling compounds in question. The following Table sets out the results obtained in these Examples and also in the comparative experiments:

TABLE

| Example No. | Enzyme | coupling compound | 1-allyloxy-3-(N-ethyleneimino)-propan-2-ol | activity U/g lyophilizate maleic anhydride | allyl bromide | acryloyl chloride | maleic acid azide |
|---|---|---|---|---|---|---|---|
| 3 – 6 | glucose oxidase | with | 360 | 110 | 260 | | 240 |
|  |  | without | 110 | 70 | 110 | | 110 |
| 7, 8 | trypsin | with |  | 6 |  | | 7.8 |
|  |  | without |  | 0.6 |  | | 0.5 |
| 9, 10 | chymotrypsin | with | 3.0 |  |  | | 0.5 |
|  |  | without | 0.1 |  |  | | 0.1 |
| 11 | uricase | with |  |  |  | 5.5 |  |
|  |  | without |  |  |  | 3.5 |  |
| 12 | hexo- | with |  |  |  | 40 |  |

TABLE-continued

| Example No. | Enzyme | coupling compound | 1-allyl-oxy-3-(N-ethylene-imino)-propan-2-ol | activity U/g lyophilizate maleic anhydride | allyl bromide | acryloyl chloride | maleic acid azide |
| --- | --- | --- | --- | --- | --- | --- | --- |
| | kinase | without | | | | 20 | |

EXAMPLE 13

The process according to Example 1 was repeated but with the use of hexokinase as protein. The polymerization system consisted of starch allyl ether, acrylamide and N,N-methylene-bis-acrylamide. The product obtained contained 120 U/g of lyophilizate.

It will be understood that the specification and examples are illustrative but not limitative of the present invention and that other embodiments within the spirit and scope of the invention will suggest themselves to those skilled in the art.

What is claimed is:

1. Process for the preparation of a carrier-bound protein, which process comprises reacting a protein in aqueous solution with a compound containing at least one group capable of acylating or alkylating proteins, said group being selected from the class consisting of an ethyleneimine group, a halide group activated by unsaturation, an acid-halide group, an azide group, an acid anhydride group, an aldehyde group, and an oxazolone group; and at least one additional group capable of producing a bond with a carrier material, and reacting the reducing product with a carrier material.

2. Process as claimed in claim 1, wherein said group capable of acylating or alkylating proteins is an ethyleneimine group.

3. Process as claimed in claim 1, wherein said group capable of acylating or alkylating proteins is a halide group activated by unsaturation.

4. Process as claimed in claim 1, wherein said group capable of acylating or alkylating proteins is an acid halide group.

5. Process as claimed in claim 1, wherein said group capable of acylating or alkylating proteins is an azide group.

6. Process as claimed in claim 1, wherein said group capable of acylating or alkylating proteins is an acid anhydride group.

7. Process as claimed in claim 1, wherein said group capable of acylating or alkylating proteins is an aldehyde group.

8. Process as claimed in claim 1, wherein said group capable of acylating or alkylating proteins is an oxazolone group.

9. Process as claimed in claim 1, wherein said additional group capable of producing a bond with a carrier material is a copolymerizable double bond.

10. Process as claimed in claim 1, wherein said carrier material is produced in aqueous solution by the polymerization of at least one monomer.

11. Process as claimed in claim 10, wherein the polymerizable monomer or monomer mixture is added to the aqueous solution in which said protein was reacted, subsequent to the reaction of the protein with the coupling compound, and then polymerizing said monomer or monomer mixture.

12. Process as claimed in claim 10, wherein the monomer is selected from the group consisting of the water-soluble amide, nitrile or ester derivative of vinyl alcohol, acrylic acid or methacrylic acid and mixtures of said derivatives.

13. Process as claimed in claim 1, wherein the reaction of the protein with said compound containing said groups is effected in the presence of a polymerizable monomer or monomer mixture, and then the polymerization is carried out to incorporate into the forming polymer the protein-compound reaction product.

14. Process as claimed in claim 1, wherein said carrier material is cross-linked.

15. Process as claimed in claim 1, wherein said compound is of the formula R.CO.X, wherein X is selected from the group consisting of

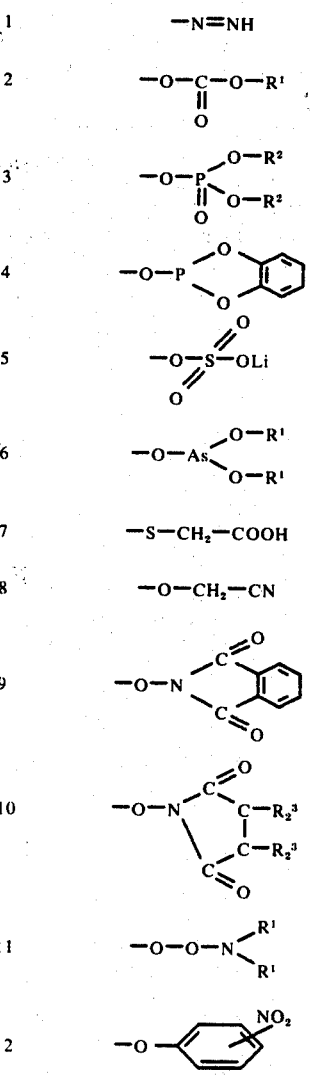

13 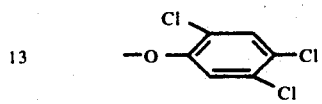

14 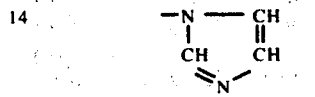

15 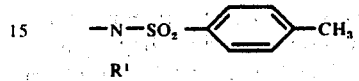

16 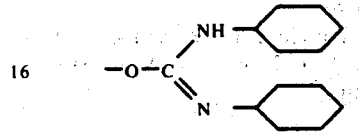

17 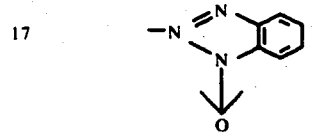

18 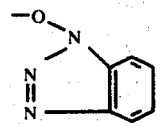

wherein
  $R^1$ is alkyl of up to 6 carbon atoms,
  $R^2$ is aryl or aralkyl of up to 12 carbon atoms or halogen atom, and
  $R^3$ is alkyl of up to 6 carbon atoms or hydrogen.

16. Process as claimed in claim 1, wherein said compound is of the formula R.CO.X, wherein X is selected from the group consisting of 19 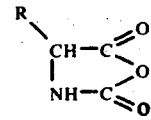

20 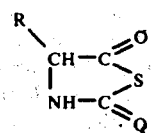

wherein R is the residue of a coupling compound which contains a functional group capable of bonding with the carrier.

17. Carrier-bound protein produced by the process claimed in claim 1.

* * * * *